United States Patent [19]

Coispeau

[11] 4,101,540
[45] Jul. 18, 1978

[54] 3-TRIFLUOROMETHYL-4-PHENYL-PYRAZOLIUM AZO DYESTUFFS

[75] Inventor: Gerard Emile Edgard Coispeau, Soisy-sous-Montmorency, France

[73] Assignee: Produits Chimiques Ugine Kuhlmann, Paris, France

[21] Appl. No.: 724,488

[22] Filed: Sep. 20, 1976

[30] Foreign Application Priority Data

Sep. 30, 1975 [FR] France .................. 75 29873
Sep. 30, 1975 [FR] France .................. 75 29874

[51] Int. Cl.² ............... C09B 29/00; C09B 29/36; C09B 29/38; D06B 3/76
[52] U.S. Cl. .................. 260/147; 260/162; 260/163; 260/465 G; 548/362
[58] Field of Search ............ 260/162, 163, 147

[56] References Cited

U.S. PATENT DOCUMENTS 2,908,677 10/1959 Straley et al. .................. 260/147
3,515,715 6/1970 Straley et al. .................. 260/163
3,948,878 4/1976 Coispeau ...................... 260/147

FOREIGN PATENT DOCUMENTS 1,486,066 5/1967 France ...................... 260/162
2,435,919 2/1975 Fed. Rep. of Germany ....... 260/162
442,569 1/1968 Switzerland .................. 260/163

Primary Examiner—Floyd D. Higel
Attorney, Agent, or Firm—Beveridge, Degrandi, Kline & Lunsford

[57] ABSTRACT

Azopyrazolium dyes of the formula:

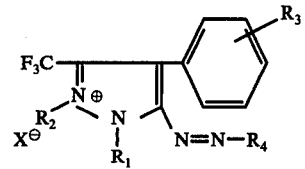

in which $R_1$ represents an alkyl group or a phenyl group which may be substituted with a halogen atom or with a nitro, alkoxy or alkyl group, $R_2$ represents an alkyl group; $R_3$ represents an atom of hydrogen or halogen; $R_4$ represents the residue of a coupler $R_4H$ free of a sulfonic or carboxylic group; and $X^-$ represents a monovalent anion, and 3-trifluoromethyl-4-aryl-5-amino pyrazoles of the formula

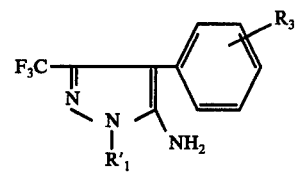

in which $R_3$ and $R_4$ have the same meanings as above and $R'_1$ represents a hydrogen atom, an alkyl group, or a phenyl group which may be substituted with a halogen atom or with a nitro, alkoxy or alkyl group, are disclosed; methods are disclosed for making these compounds and using them for the dyeing of fibers based on polymers and copolymers of acrylonitrile or on acid-modified polyesters or polyamides to pure and brilliant shades having good fastness, especially fastness to light, e.g., for using the pyrazoles to form the dyes.

7 Claims, No Drawings

3-TRIFLUOROMETHYL-4-PHENYL-PYRAZOLIUM AZO DYESTUFFS

AZOPYRAZOLIUM DYES, PYRAZOLE COMPOUNDS AND METHODS

The present invention relates to new azopyrazolium dyes, which may be utilized for the dyeing of synthetic fibers having an acidic nature, such as those based on polymers or copolymers of acrylonitrile. In a further aspect, the present invention relates to new pyrazole compounds which may be used for the preparation of these dyes. In a still further aspect, the present invention relates to methods of making the aforementioned dyes and compounds and to methods for using the dyestuffs.

The dyes according to the invention may be represented by the general formula:

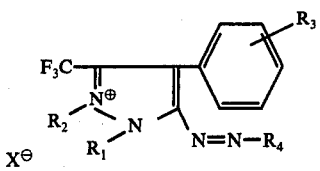

in which $R_1$ represents an alkyl group or a phenyl group which may be substituted with a halogen atom or with a nitro, alkoxy or alkyl group;

$R_2$ represents an alkyl group;

$R_3$ represents an atom of hydrogen or halogen;

$R_4$ represents the residue of a coupler $R_4H$ free of a sulfonic or carboxylic group; and $X^-$ represents a monovalent anion.

The alkyl groups preferably contain 1 to 4 carbon atoms, and the alkoxy groups 1 or 2 carbon atoms. The halogen preferably may be chloro or bromo.

The coupler of formula $R_4H$ can be any one of the couplers usually used for the synthesis of cationic azo dyes. These are known in the art and includes, for example, the series of aromatic amines such as N,N-diethyl-meta-toluidine; N,N-dimethylaniline; N,N-diethyl-meta-anisidine; N-ethyl-N-cyanoethyl-aniline; N,N-diethyl-N'-acetyl-meta-phenylenediamine; N,N-diethyl-2,5-diethoxyaniline; N,N-dimethyl-2,5-dimethylaniline; N-(2-diethylaminoethyl)-N-ethyl-meta-toluidine; N-trifluoroethyl-N-ethyl-meta-toluidine; N-ethyl-N-succinimidoethyl-meta-toluidine; N,N-diethylmeta-chloroaniline; N-ethyl-N-cyanoethyl-meta-toluidine; N-phenylmorpholine; N-methyl-diphenylamine; and N-(para-methoxyphenyl)alpha-naphthylamine.

Further, examples of couplers $R_4H$ include heterocyclic compounds such as:
indoles of formula:

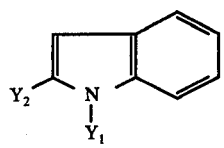

in which $Y_1$ represents a hydrogen atom or an alkyl, cyanoalkyl, hydroxyalkyl or phenyl group and $Y_2$ represents an atom of hydrogen or an alkyl or phenyl group, such as indole, 2-methyl indole, 2-phenyl indole, 1-methyl-2-phenyl indole, 1-ethyl-2-methyl-indole, 1-cyanoethyl-2-methyl indole, 1-cyanoethyl-2-phenyl indole, 2-isopropyl indole, 1-(2-hydroxypropyl)-2-phenyl indole, and -pyrazolones of formula:

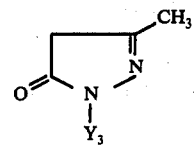

in which $Y_3$ represents a hydrogen atom or a phenyl group which may be substituted with a halogen atom or with a nitro, alkyl or alkoxy group, such as 3-methyl-5-pyrazolone, 1-phenyl-3-methyl-5-pyrazolone, 1-p-tolyl-3-methyl-5-pyrazolone, 1-m-nitrophenyl-3-methyl-5-pyrazolone, 1-p-chloro-phenyl-3-methyl-5-pyrazolone, and 1-p-methoxyphenyl-3-methyl-5-pyrazolone.

The dyes of formula (I) may be prepared by treating with alkylating agents compounds of the general formula:

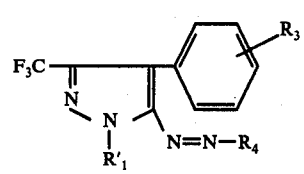

in which $R_3$ and $R_4$ have the same meanings as above and $R'_1$ represents a hydrogen atom, an alkyl group, or a phenyl group which may be substituted with a halogen atom or with a nitro, alkoxy or alkyl group.

The alkylating treatment can be carried out in inert organic solvents, such as benzene hydrocarbons and their chlorinated derivatives, dimethylformamide, or chloroform; or likewise in an excess of alkylating agent. As alkylating agent, there may be used, for example, alkyl halides, alkyl arylsulfonates, alkyl sulfates, and in particular the methyl and ethyl compounds.

The compounds of formula (IV) may be prepared by coupling the diazo derivative of a 3-trifluoromethyl-4-aryl-5-aminopyrazole of general formula:

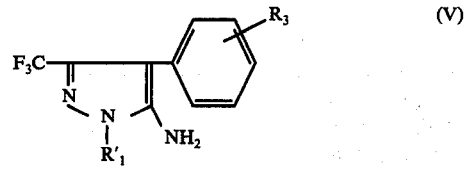

with a coupling compound $R_4H$, wherein $R'_1$, $R_3$ and $R_4$ having the same meanings as above.

Diazotization of the aminopyrazoles of formula (V) is carried out in presence of an organic acid of low molecular weight such as the carboxylic acids, acetic or propionic acid or in the presence of concentrated mineral acid.

When used for the dyeing of selected synthetic fibers, dyes of formula (I) confer pure and brilliant shades having good fastness, especially fastness to light. Selected synthetic fibers include fibers based on polymers and copolymers of acrylonitrile as well as fibers based on polyesters or on polyamides modified by acid groups.

Dyeing is effected by the dye cation; the anion plays no tinctorial role. Therefore the anion (x) may vary widely as is known in the art. It can be changed for another anion, for example with a view to improving the solubility of the dyes. Examples of anions include chloride, sulphomethylate, sulphoethylate, chlorozincate, acetate, nitrate, bicarbonate, p-toluenesulphonate.

The 3-trifluoromethyl-4-aryl-5-aminopyrazoles of formula (V) are new compounds and, as such, form another aspect of the present invention. These compounds may be prepared by condensation of a hydrazine of formula:

$$R'_1 - NH - NH_2 \qquad (VI)$$

with a beta-ketonitrile of formula:

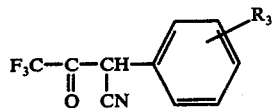

$R'_1$ and $R_3$ having the same meanings as above.

This condensation reaction is preferably carried out in the presence of an inert organic solvent such as an alcohol, a benzene hydrocarbon or its chlorinated derivative, dimethylformamide, or chloroform.

Beta-ketonitriles of formula (VII) may be prepared according to the method described by W. R. Nes and A. Burger, Jour. Amer. Chem. Soc. (1950), 72, 5408.

In the examples below, which illustrate the invention, the parts indicated are by weight.

EXAMPLE 1

4.4 parts of 3(5)-trifluoromethyl-4-phenyl-5(3)-aminopyrazole are dissolved in 28 parts of concentrated sulfuric acid. The solution is cooled to between 0° and 5° C and there is then added to it a solution of 1.45 parts of sodium nitrite in 28 parts of concentrated sulfuric acid. Stirring is continued for one half hour. The sulfuric acid solution of the diazo derivative thus obtained is then gradually added to a solution of 3.2 parts of N,N-diethyl-meta-toluidine in 60 parts of water and 1.8 parts of sulfuric acid. To complete the coupling, the mixture is progressively brought to pH 4 by addition of ammonia. The precipitate is then filtered, washed with water and dried.

Four parts of the 5(3)-(4-diethylamino-2-methyl-phenylazo)-4-phenyl-3(5)-trifluoromethylpyrazole thus obtained are introduced into 26 parts of methyl sulfate. Heating at 100° C is carried out until a test sample is completely soluble in water, then after the mixture has cooled to ambient temperature, 25 parts of water are added and it is permitted to stand with stirring for one half hour at 60° C. The dye is then precipitated by addition of sodium chloride and zinc chloride, filtered and dried.

The 1,2-dimethyl-3-trifluoromethyl-4-phenyl-5-(4-diethylamino-2-methyl-phenylazo)-pyrazolium chlorozincate thus obtained dyes fibers based on polymers or copolymers of acrylonitrile to a bright bluish-red shade which is remarkably fast to light.

Table A following sums up other examples of dyes according to the invention prepared as in the preceding example, starting with the same diazo derivative but replacing the N,N-diethyl-meta-toluidine by the coupler $R_4H$ indicated in the second column.

| Ex. | Coupler $R_4H$ | Shade on acrylic fibers |
|---|---|---|
| 2 | N,N-dimethylaniline | red |
| 3 | N,N-diethyl-meta-anisidine | red |
| 4 | N-ethyl-N-(β-cyanoethyl)-aniline | scarlet |
| 5 | N-ethyl-N-(β-cyanoethyl)-meta-toluidine | scarlet |
| 6 | N,N-diethyl-2,5-diethoxyaniline | bluish red |
| 7 | N,N-dimethyl-2,5-dimethylaniline | bluish red |
| 8 | N-(2-diethylaminoethyl)-N-ethyl-meta-toluidine | scarlet |
| 9 | N-(2,2,2-trifluoroethyl)-N-ethyl-meta-toluidine | scarlet |
| 10 | N-(2-succinimidoethyl)-N-ethyl-meta-toluidine | bluish red |
| 11 | N-phenyl morpholine | scarlet |
| 12 | 1-methyl-2-phenylindole | yellow |
| 13 | 1-β-cyanoethyl-2-phenylindole | yellow |
| 14 | 1-phenyl-3-methyl-5-pyrazolone | yellow |

Table B, below sums up other examples of dyes according to the invention, obtained by following the procedure of example 1 but with the 3(5)-trifluoromethyl-4-phenyl-5(3)-amino-pyrazole replaced by an equimolar quantity of the aminopyrazole indicated in the second column and/or the N,N-diethyl-meta-toluidine by an equimolar quantity of the coupler indicated in the third column.

TABLE B

| Ex. | Aminopyrazole of formula (V) | Coupler of formula $R_4H$ | Shade on acrylic fibers |
|---|---|---|---|
| 15 | 1,4-diphenyl-3-trifluoromethyl-5-aminopyrazole | N,N-diethyl-meta-toluidine | bluish-red |
| 16 | 1,4-diphenyl-3-trifluoromethyl-5-aminopyrazole | N,N-diethyl-m-chloroaniline | bluish-red |
| 17 | 1-p-nitrophenyl-3-trifluoromethyl-4-phenyl-5-aminopyrazole | N,N-diethyl-m-toluidine | bluish-red |
| 18 | 1-p-chlorophenyl-3-trifluoromethyl-4-phenyl-5-aminopyrazole | N,N-diethyl-m-chloroaniline | bluish-red |
| 19 | 1-p-tolyl-3-trifluoromethyl-4-phenyl-5-aminopyrazole | N,N-diethyl-m-chloroaniline | bluish-red |
| 20 | 3(5)-trifluoromethyl-4-p-chlorophenyl-5(3)-aminopyrazole | N,N-diethyl-m-chloroaniline | bluish-red |
| 21 | 1-phenyl-3-trifluoromethyl-4-p-chlorophenyl-5-aminopyrazole | N,N-diethyl-m-chloroaniline | bluish-red |
| 22 | 1-phenyl-3-trifluoromethyl-4-m-chlorophenyl-5-aminopyrazole | N,N-diethyl-m-chloroaniline | bluish-red |

EXAMPLE 23

Synthesis of 3(5)-trifluoromethyl-4-phenyl-5(3)-aminopyrazole.

To 20 parts of 2-phenyl-2-trifluoroacetyl-acetonitrile in solution in 105 parts of benzene and 8 parts of acetic acid are added 6 parts of hydrazine hydrate. This mixture is refluxed for 3 hours, then the benzene is distilled off. The oily mass obtained precipitates gradually. The 3(5)-trifluoromethyl-4-phenyl-5(3)-aminopyrazole thus obtained, after recrystallization in water, is a white product which melts at 116° C.

| Analysis | C% | H% | F% | N% |
|---|---|---|---|---|
| Calculated for $C_{10}H_8F_3N_3$... | 52.86 | 3.55 | 25.09 | 18.50 |
| Found... | 52.91 | 3.45 | 25.32 | 18.32 |

Table C, below, contains other examples of compounds of formula (V) where $R_3$ represents hydrogen and $R'_1$ has the meaning indicated in the second column of the table. They are obtained by following the same procedure in example 23, but with the hydrazine hydrate replaced by an equimolar quantity of the corresponding hydrazine of formula (VI).

TABLE C

| Ex. | R₁' | M.P. °C | Analysis | | | |
|---|---|---|---|---|---|---|
| | | | | C% | H% | N% |
| 24 | phenyl | 106 | Calc. | 63.36 | 3.99 | 13.86 |
| | | | Found | 63.01 | 3.97 | 13.86 |
| 25 | methyl | 90 | Calc. | 54.77 | 4.18 | 17.42 |
| | | | Found | 54.68 | 4.09 | 17.61 |
| 26 | p-nitrophenyl | 112 | Calc. | 55.18 | 3.18 | 16.09 |
| | | | Found | 55.04 | 3.14 | 16.84 |
| 27 | p-methoxyphenyl | 97 | Calc. | 61.26 | 4.23 | 12.61 |
| | | | Found | 61.01 | 4.19 | 12.48 |
| 28 | p-chlorophenyl | 115 | Calc. | 56.90 | 3.28 | 12.44 |
| | | | Found | 57.37 | 3.32 | 12.49 |
| 29 | p-tolyl | 105 | Calc. | 64.35 | 4.45 | 13.24 |
| | | | Found | 64.04 | 4.46 | 13.15 |

Table D below contains other examples of compounds of formula (V) where R'₁ and R₃ have the meanings indicated in the second and third columns of the table. They are obtained by following the same procedure as in example 23, but with the 2-phenyl-2-trifluoroacetyl-acetonitrile replaced by an equimolar quantity of the corresponding beta-ketonitrile of formula (VII), and with the hydrazine hydrate replaced by an equimolar quantity of the corresponding hydrazine of formula (VI).

TABLE D

| Ex. | R'₁ | R₃ | M.P. °C | Analysis | | | |
|---|---|---|---|---|---|---|---|
| | | | | | C% | H% | N% |
| 30 | H | 4-chloro | 140 | Calc. | 45.91 | 2.70 | 16.06 |
| | | | | Found | 45.78 | 2.73 | 15.87 |
| 31 | phenyl | 4-chloro | 105 | Calc. | 56.90 | 3.28 | 12.44 |
| | | | | Found | 56.69 | 3.33 | 12.18 |
| 32 | p-chloro-phenyl | 4-chloro | 106 | Calc. | 51.63 | 2.71 | 11.29 |
| | | | | Found | 51.74 | 2.78 | 11.19 |
| 33 | methyl | 4-chloro | 104 | Calc. | 47.93 | 3.29 | 15.24 |
| | | | | Found | 48.11 | 3.33 | 14.86 |
| 34 | phenyl | 3-chloro | 70 | Calc. | 56.90 | 3.28 | 12.44 |
| | | | | Found | 56.37 | 3.42 | 12.09 |

I claim:
1. A dyestuff of the formula:

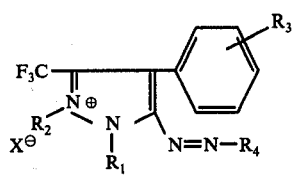

in which R₁ is alkyl containing 1 to 4 carbon atoms, phenyl, chlorophenyl, bromophenyl, nitrophenyl, alkoxy (C₁-C₂)-phenyl or alkyl (C₁-C₄)-phenyl;
R₂ is alkyl containing 1 to 4 carbon atoms;
R₃ is hydrogen, chlorine or bromine;
R₄ is a radical of the formula:

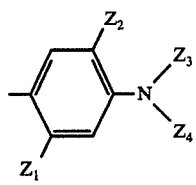
(a)

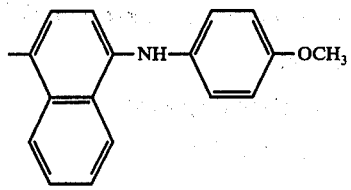
(b)

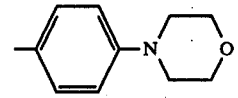
(c)

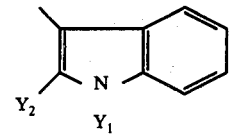
(d)

or

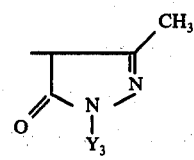
(e)

Y₁ is hydrogen, methyl, ethyl, cyanoethyl or 2-hydroxypropyl;
Y₂ is hydrogen, methyl, isopropyl or phenyl;
Y₃ is hydrogen, phenyl, tolyl, nitrophenyl, chlorophenyl or methoxyphenyl;
Z₁ is hydrogen, chlorine, methyl, methoxy, ethoxy or acetylamino;
Z₂ is hydrogen, methyl or ethoxy;
Z₃ is methyl or ethyl;
Z₄ is methyl, ethyl, cyanoethyl, trifluoroethyl, diethylaminoethyl, succinimidoethyl or phenyl; and
X⊖ is a monovalent anion.

2. A dyestuff of the formula:

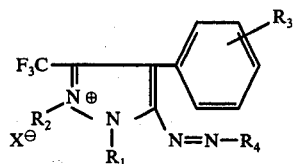

in which R₁ is alkyl containing 1 to 4 carbon atoms, phenyl, chlorophenyl, bromophenyl, nitrophenyl, alkoxy (C₁-C₂)-phenyl or alkyl (C₁-C₄)-phenyl;
R₂ is alkyl containing 1 to 4 carbon atoms;
R₃ is hydrogen, chlorine or bromine;
R₄ is 4-diemethylamino-phenyl,
4-diethylamino-2-methyl-phenyl,
4-diethylamino-2-methoxy-phenyl,
4-(N-ethyl-N-cyanoethylamino)-phenyl,
2-acetylamino-4-diethylamino-phenyl,
2,5-diethoxy-4-diethylamino-phenyl,
2,5-dimethyl-4-dimethylamino-phenyl,
4-[N-2-diethylaminoethyl)-N-ethylamino]-2-methyl-phenyl,
2-methyl-4-(N-trifluoroethyl-N-ethylamino)-phenyl,
2-methyl-4-(N-ethyl-N-succinimidoethylamino)-phenyl,
2-chloro-4-diethylamino-phenyl, 4-(N-ethyl-N-cyanoethylamino)-2-methyl-phenyl, 4-morpholino-phenyl, 4-(N-methyl-N-phenylamino)-phenyl, 4-(4-methoxy-anilino)-1-naphtyl, 3-indolyl, 2-methyl-3-indolyl, 2-phenyl-3-indolyl, 1-methyl-2-phenyl-3-indolyl, 1-ethyl-2-methyl-3-indolyl, 1-cyanoethyl-2-methyl-3-indolyl, 1-cyanoethyl-2-phenyl-3-indolyl, 2-isopropyl-3-indolyl, 1-(2-hydroxypropyl)-2-phenyl-3-indolyl, 3-methyl-5-hydroxy-4-pyrazolyl, 1-phenyl-3-methyl-5-hydroxy-4-pyrazolyl, 1-p-tolyl-3-methyl-5-hydroxy-4-pyrazolyl, 1-m-nitrophenyl-3-methyl-5-hydroxy-4-pyrazolyl, 1-p-chlorophenyl-3-methyl-5-hydroxy-4-pyrazolyl, or 1-p-methoxyphenyl-3-methyl-5-hydroxy-4-pyrazolyl, and X<sup>⊖</sup> is a monovalent anion.

3. The dyestuff according to claim 1 having the formula:

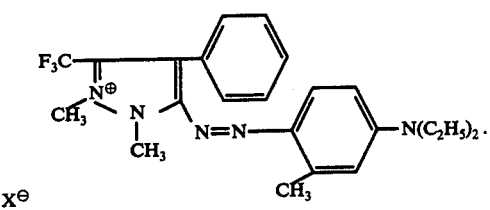

4. The dyestuff according to claim 1 having the formula:

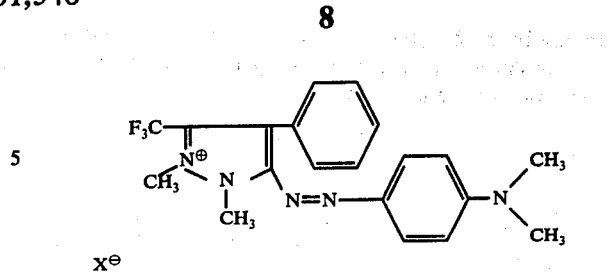

5. The dyestuff according to claim 1 having the formula:

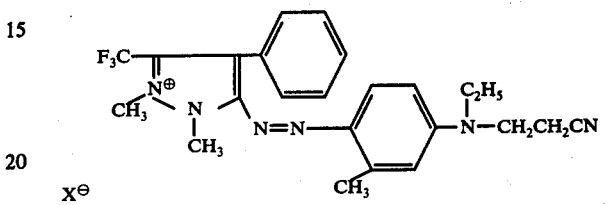

6. The dyestuff according to claim 1 having the formula:

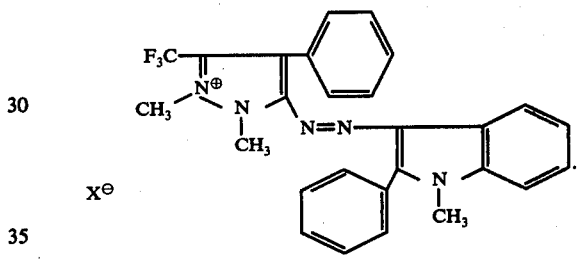

7. The dyestuff according to claim 1 having the formula:

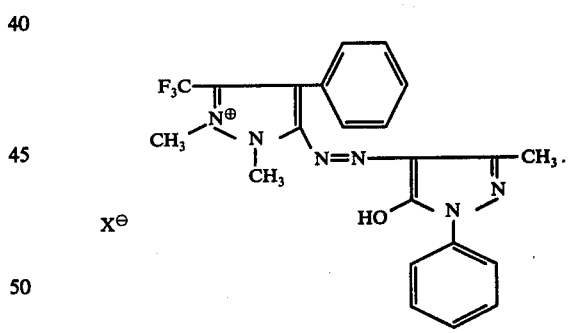

* * * * *